(12) United States Patent
Giles et al.

(10) Patent No.: US 9,687,093 B2
(45) Date of Patent: Jun. 27, 2017

(54) PATIENT WARMING BLANKET, DRAPE, AND CORRESPONDING PATIENT WARMING SYSTEM

(75) Inventors: Andrew James Giles, Libertyville, IL (US); Francis Anthony Czajka, Libertyville, IL (US); Tim Finnigan, Libertyville, IL (US); John Henry Kutsch, Harvard, IL (US); Vince R. Lackowski, Glenview, IL (US)

(73) Assignee: Medline Industries, Inc, Northfield, IL (US)

( * ) Notice: Subject to any disclaimer, the term of this patent is extended or adjusted under 35 U.S.C. 154(b) by 1152 days.

(21) Appl. No.: 13/116,749

(22) Filed: May 26, 2011

(65) Prior Publication Data

US 2012/0298117 A1    Nov. 29, 2012

(51) Int. Cl.
| | | |
|---|---|---|
| *A61F 7/08* | (2006.01) | |
| *A61B 19/08* | (2006.01) | |
| *A47G 9/02* | (2006.01) | |
| *A61F 7/00* | (2006.01) | |
| *A61B 46/00* | (2016.01) | |
| *A61F 7/02* | (2006.01) | |

(52) U.S. Cl.
CPC ............ *A47G 9/0215* (2013.01); *A61B 46/00* (2016.02); *A61B 46/40* (2016.02); *A61F 7/0097* (2013.01); *A61F 2007/0255* (2013.01)

(58) Field of Classification Search
USPC .................................................. 128/849–856
See application file for complete search history.

(56) References Cited

U.S. PATENT DOCUMENTS

| | | | |
|---|---|---|---|
| 3,500,014 A | | 3/1970 | Santo |
| 4,284,680 A | | 8/1981 | Awano et al. |
| 4,569,874 A | * | 2/1986 | Kuznetz ........................ 428/109 |
| 4,622,253 A | | 11/1986 | Levy |
| 4,765,323 A | | 8/1988 | Poettgen |
| 4,945,924 A | | 8/1990 | Poettgen |
| 4,988,053 A | | 1/1991 | Choi |

(Continued)

FOREIGN PATENT DOCUMENTS

| | | |
|---|---|---|
| JP | 2004-168008 | 6/2004 |
| JP | 3136000 | 9/2007 |

OTHER PUBLICATIONS

"Publicaiton", *3M Product Information—Bair Hugger Therapy, Underbody Series Blankets*, Published 2011 by Arizant Healthcare Inc.; 4 pages.

(Continued)

*Primary Examiner* — Kari Rodriquez
(74) *Attorney, Agent, or Firm* — Philip H. Burrus, IV

(57) ABSTRACT

A patient warming device (400), which can be configured as a patient warming blanket (207), patient warming drape (300), or surgical drape (500), includes the top layer of material and optionally a bottom layer of material. The top layer (401) can be formed by laminating non-woven fabric (301) to a film layer (100) or by needle punching fibers through the film layer (100). The film layer (100) has a thermally reflective side (404) and a thermally absorptive side (405). The patient warming device (400) can be used in a patient warming system (700) with one or more light sources (701,702) and an optional control module (704) to warm a patient during and after medical procedures.

16 Claims, 9 Drawing Sheets

(56) References Cited

U.S. PATENT DOCUMENTS

| | | | |
|---|---|---|---|
| 5,038,779 | A | 8/1991 | Barry et al. |
| 5,125,238 | A | 6/1992 | Ragan et al. |
| 5,780,367 | A | 7/1998 | Handwerker |
| 6,331,695 | B1 | 12/2001 | West |
| 6,440,159 | B1 | 8/2002 | Edwards et al. |
| 6,610,928 | B2 | 8/2003 | Synder |
| 6,770,848 | B2 | 8/2004 | Haas et al. |
| 7,837,721 | B2 | 11/2010 | Augustine et al. |
| 7,931,682 | B2 | 4/2011 | Albrecht et al. |
| 7,976,572 | B2 | 7/2011 | Ziaimehr |
| 8,453,264 | B2 * | 6/2013 | Mickle et al. ............ 2/82 |
| 2004/0096620 | A1 | 5/2004 | Dillinger |
| 2006/0101558 | A1 | 5/2006 | Coleman et al. |
| 2006/0135019 | A1 | 6/2006 | Russell |
| 2006/0178717 | A1 | 8/2006 | Harris et al. |
| 2006/0253954 | A1 | 11/2006 | Music |
| 2008/0203080 | A1 | 8/2008 | Fung |
| 2009/0209155 | A1 | 8/2009 | Goulet |
| 2009/0217440 | A1 | 9/2009 | Sutker |
| 2010/0089897 | A1 | 4/2010 | Bart |
| 2010/0263104 | A1 | 10/2010 | Flannery |
| 2011/0108538 | A1 | 5/2011 | Gray |
| 2011/0302690 | A1 | 12/2011 | Cox et al. |

OTHER PUBLICATIONS

"Publication", "*Hot Dog Warming System*"; Product catalogue; Published 2012 by Augustine Temperature Management; 2 pages.
"Publication", "*Koala Warming System*" Product Brochure; Published 2011 by NovaMed USA; 4 pages.
"Publication", "*Bair Paws+Gown*"—Product Brochure; 3M; Published 2012 by Arizant Healthcare Inc.
Kamath, M. G., et al., "Needle Punched Nonwovens", *NPL Document* M.G. Kamath Atul Dahiya Radhavendra R Hegde (Praveen Jana & Xinli Liu) Updated Apr. 12, 2010.
Sook, Cho Y., "International Search Report", PCT/US2012/032149; Filed Apr. 4, 2012; Mailed Oct. 30, 2012.
Jackson, Brandon L., "NonFinal OA", U.S. Appl. No. 13/585,435, filed Aug. 14, 2012; Mailed Mar. 28, 2013.
Jackson, Brandon L., "Final OA", U.S. Appl. No. 13/585,435, filed Aug. 14, 2012; Mailed Oct. 23, 2013.
Yang, In Su "PCT Search Report and Written Opinion", PCT/US2013/053397; Filed Aug. 2, 2013; Mailed Nov. 15, 2013.
Jackson, Brandon "Appeal Decision", U.S. Appl. No. 13/585,435, filed Aug. 14, 2012; Mailed Dec. 1, 2016.
"Medline Catalog", *Bair Hugger Full Body Blankets by Arizan*; Medline Catalog; http://www.medline.com/catalog/catalog.jsp; Unknown Publication date but believed to be prior to present application filing date.
"Medline Catalog", *Bair Paws Flex Warming Gowns by 3M Healthcare*; Medline Catalog; http://www.medline.com/catalog/catalog.jsp; Unknown Publication date but believed to be prior to present application filing date.
"Medline Catalog", *Bair Paws Patient Warming Gown kits by 3M Healthcare*; Medline Catalog; http://www.medline.com/catalog/catalog.jsp; Unknown Publication date but believed to be prior to present application filing date.
"Medline Catalog", *Blankets by Smiths Medical*; Medline Catalog; http://www.medline.com/catalog/catalog.jsp; Unknown Publication date but believed to be prior to present application filing date.
"Medline Catalog", *Delta Pediatric Overlays by Span America*; Medline Catalog; http://www.medline.com/catalog/catalog.jsp; Unknown Publication date but believed to be prior to present application filing date.
"Medline Catalog", *Disposable Hypothermia Blankets* by Cincinnati Sub Zero; Medline Catalog; http://www.medline.com/catalog/catalog.jsp; Unknown Publication date but believed to be prior to present application filing date.
"Medline Catalog", *FilteredFlo Warming Tube* by Cincinnati Sub Zero; Medline Catalog; http://www.medline.com/catalog/catalog.jsp; Unknown Publication date but believed to be prior to present application filing date.
"Medline Catalog", *Maxi-therm Blanket* by Cincinnati Sub-zero; Medline Catalog; http://www.medline.com/catalog/catalog.jsp; Unknown Publication date but believed to be prior to present application filing date.
"Medline Catalog", *Mistral-Air Forced Air Warming Blankets* by Stryker; Medline Catalog; http://www.medline.com/catalog/catalog.jsp; Unknown Publication date but believed to be prior to present application filing date.
"Medline Catalog", *Patient Warming System* by Halyard Health; Medline Catalog; http://www.medline.com/catalog/catalog.jsp; Unknown Publication date but believed to be prior to present application filing date.
"Medline Catalog", *Soft-Temp Heat Therapy Pads/Parts* by Adroit Medical; Medline Catalog; http://www.medline.com/catalog/catalog.jsp; Unknown Publication date but believed to be prior to present application filing date.
"Medline Catalog", *Warming Blankets by Covidien*; Medline Catalog; http://www.medline.com/catalog/catalog.jsp; Unknown Publication date but believed to be prior to present application filing date.
Hawthorne, Ophelia Althea "Notice of Allowance", U.S. Appl. No. 13/585,435, filed Aug. 14, 2012; Mailed Jan. 6, 2017.

* cited by examiner

PATIENT WARMING BLANKET, DRAPE, AND CORRESPONDING PATIENT WARMING SYSTEM

BACKGROUND

Technical Field

This invention relates generally to blankets, and more particularly to a warming blanket suitable for use by patients undergoing medical procedures.

Background Art

Patients undergoing surgery or other medical procedures can experience significant drops in body temperature, both while under the affect of anesthesia and while recovering. Many medical procedures—from routine endoscopies to complex surgeries—can last more than an hour with the patient sedated with anesthesia. During such procedures, the patient's core body temperature can drop up to 1.7 degrees centigrade due to anesthetization. Clinical studies have shown that mitigating this temperature drop can have positive effects after the procedure. Benefits of preventing significant temperature drop include lower risk of infection after the operation, faster healing, and lower incidents of excessive bleeding.

Preventing core temperature drop is not a trivial task. One cannot simply "turn up the thermostat" in the operating room. To prevent an anesthetized patient from cooling, the necessary room temperature would not only cause medical personnel to be uncomfortable, but could even prevent them from doing their jobs properly. Prior patient warming attempts have been cumbersome and expensive. For example, U.S. Pat. No. 5,125,238 to Ragan et al. describes a disposable patient heating blanket where multiple layers form an air chamber. A complex series of blowers, heating devices, cooling devices, and so forth are then connected to the device. This complex network of machines then introduces conditioned air into the chamber. The problem with such devices, aside from cost and complexity, is that the necessary tubes, conduits, and machines frequently get in the way during a medical procedure. Additionally, the machinery is noisy and can disrupt communication during the medical procedure.

It would be advantageous to have a more effective and lower cost patient warming device.

Figure 1:
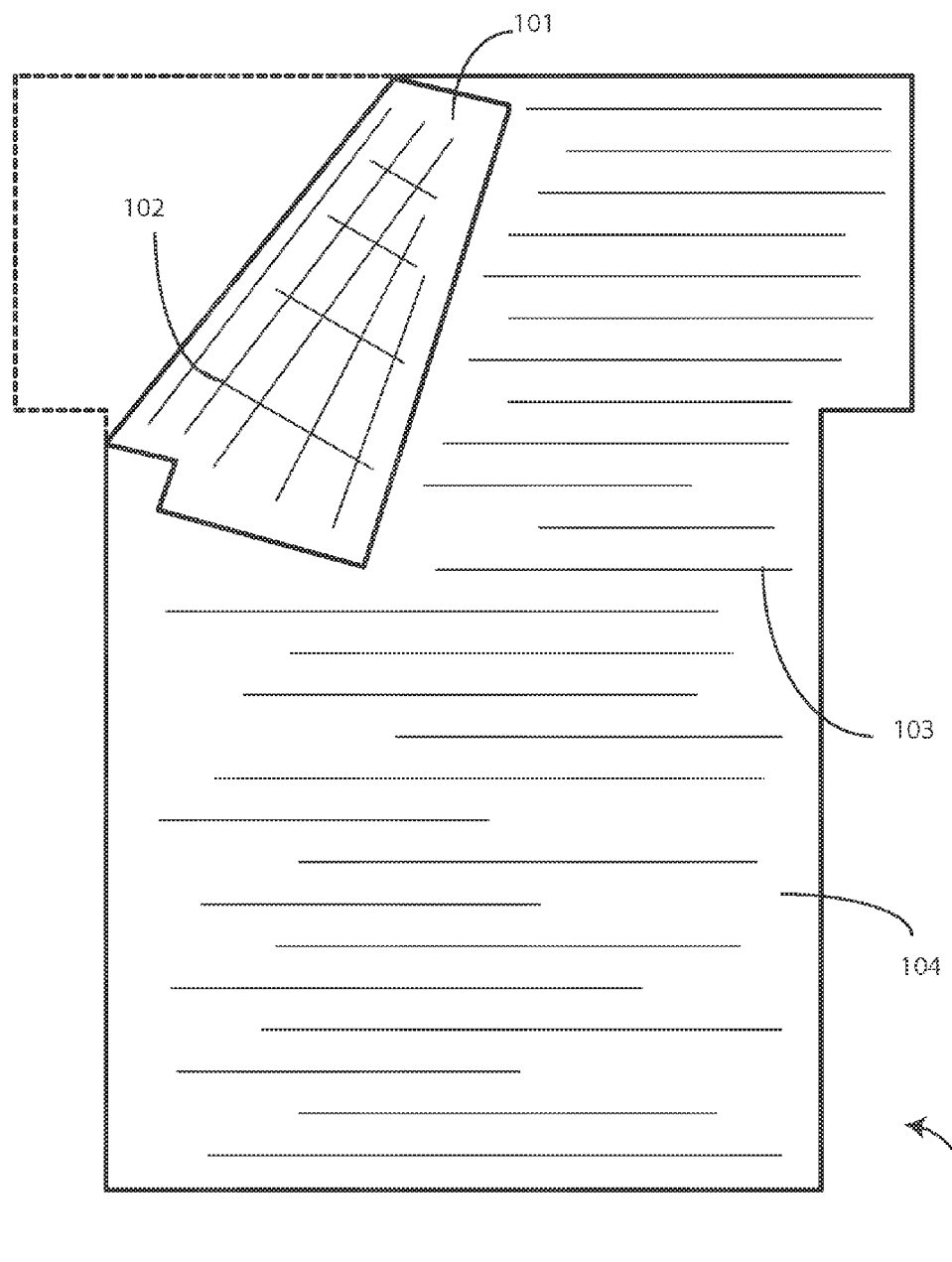
FIG. 1 illustrates one illustrative film layer suitable for use with blankets and drapes configured in accordance with one or more embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the invention described herein provide patient warming blankets and drapes that are configured with both thermally reflective and thermally absorptive properties that are used to maintain a sufficiently elevated patient core body temperature both during and after medical procedures and surgeries. The thermally reflective properties reflect the patient's body heat back to the patient, while the thermally absorptive properties convert light to heat to help warm the patient during and after procedures in addition to preventing heat loss.

In one embodiment, a patient warming blanket includes a film layer having a thermally reflective feature on at least one side. A thermally absorptive material is disposed opposite the thermally reflective side. A blanket can then be formed by needle-punching non-woven material through the film layer in a needle punch process. This technique produces a patient warming blanket that maintains a very soft and "drapable" feel. However, experimental testing has shown that this embodiment of the invention is in excess of 25% better than a standard blanket normally used in medical procedures across time.

Embodiments of the patient warming blanket can be cut into various shapes and sizes, as desired, and can be used in targeted zones along the patient to provide reflective heat retention and absorptive heat capture along areas of the body outside the actual surgical zone. Illustrating by way of example, a patient undergoing a lower-body surgical procedure may have the patient warming blanket disposed along their upper body during the procedure. Additionally, embodiments of the invention can be used with or under traditional surgical drapes.

In another embodiment, a patient warming drape is formed by laminating a non-woven material to a film layer having a thermally reflective side and a thermally absorptive side. In one embodiment, the thermally absorptive side is formed by applying an ultra matte black coating, which can be a paint, polymerized coating, rubberized coating, plasticized coating, lacquer, or other material along one side of the film layer. The black coating is configured to absorb radiant energy from either existing lights or a specially configured incandescent or ultraviolet lamp configured for use with the drape. Lamps configured to emit a specific wavelength of light corresponding to specific absorption properties of the thermally absorptive coating can be used as well. The thermally absorptive side absorbs the light and, in turn, converts the received light into heat to warm the patient.

In one embodiment, the patient warming drape or blanket can be used as a stand-alone blanket or drape. In another embodiment, the blanket or drape can be used with specially configured light sources that are configured to deliver light to the absorptive coating for conversion to thermal energy. A control device can be configured to selectively vary the amount of light delivered to the patient, such as by varying the duty cycle of the light, intensity of the light, and so forth.

In one embodiment, the reflective side of the film layer is left exposed along the patient side of the blanket or drape. This configuration means that maximum reflection of the patient's body heat will occur with the thermally absorptive material adding to the warming capabilities of the device. In one embodiment, a drape can be configured with a predefined fenestration through which a surgeon may conduct a procedure. The film layer, reflective material, and/or thermally absorptive material can be selectively placed only along portions of the overall blanket or drape to provide heating properties only in selected areas. For example, where a fenestration is included in a drape, the film layer may be separated from the fenestration window by a separation region that is only non-woven material. This separation region may be three to four inches wide, for example, to avoid possible arcing of any electrocautery device that may be used in the surgical procedure. In one embodiment, the drape or blanket is combined with a reflective cover that can be placed beneath the patient to provide a complete reflective "cocoon."

Turning now to FIG. 1, illustrated therein is one embodiment of a film layer 100 suitable for use with patient warming blankets, drapes, and systems described herein. The film layer 100 forms a core layer for the blankets and drapes described below. The film layer 100 is flexible and pliable enough to be incorporated into a blanket or drape without significantly detracting from the feel, flexibility, and "drapability" of conventional blankets and drapes.

The film layer 100 can be manufactured from a variety of materials, including metalized materials or thermoplastic materials. Examples include polyethylene films, polypropylene films, polyester films, or polybutylene films. In one embodiment the film layer 100 comprises a sheet of polyester-type film. For example, in one embodiment the film layer 100 can be manufactured from polyethelyene terephthalate. Polyethelyene terephthalate, which is also known as PTE or PETE, is a thermoplastic polymer resin that can exist as an amorphous, substantially transparent film. One advantage associated with polyethelyene terephthalate is that it provides—in addition to thermal properties—moisture barrier properties as well.

Another advantage of such thermoplastic materials is that polyethelyene terephthalate can be aluminized as a film. In one or more embodiments of the invention described below, the film layer 100 includes at least one reflective side 101. Aluminizing polyethelyene terephthalate is one way of achieving a reflective side 101 along the film layer 100. In a metalizing process, a reflective metal, such as aluminum, can be evaporated along the film layer 100 to make one or both sides of the film layer 100 reflective. It will be clear to those of ordinary skill in the art having the benefit of this disclosure that other metals, such as gold or silver, can be substituted for the aluminum in the metalizing process.

In another embodiment, the film layer 100 can be manufactured from Mylar. Mylar is a trade name for biaxially oriented polyethelyene terephthalate film. Mylar is well suited for use as the film layer because it too can be metalized to form the reflective side 101. Further, both Mylar and generic polyethelyene terephthalate exhibit very high tensile strengths without disrupting the flexible feel of a drape or blanket into which they are integrated.

Figure 6:
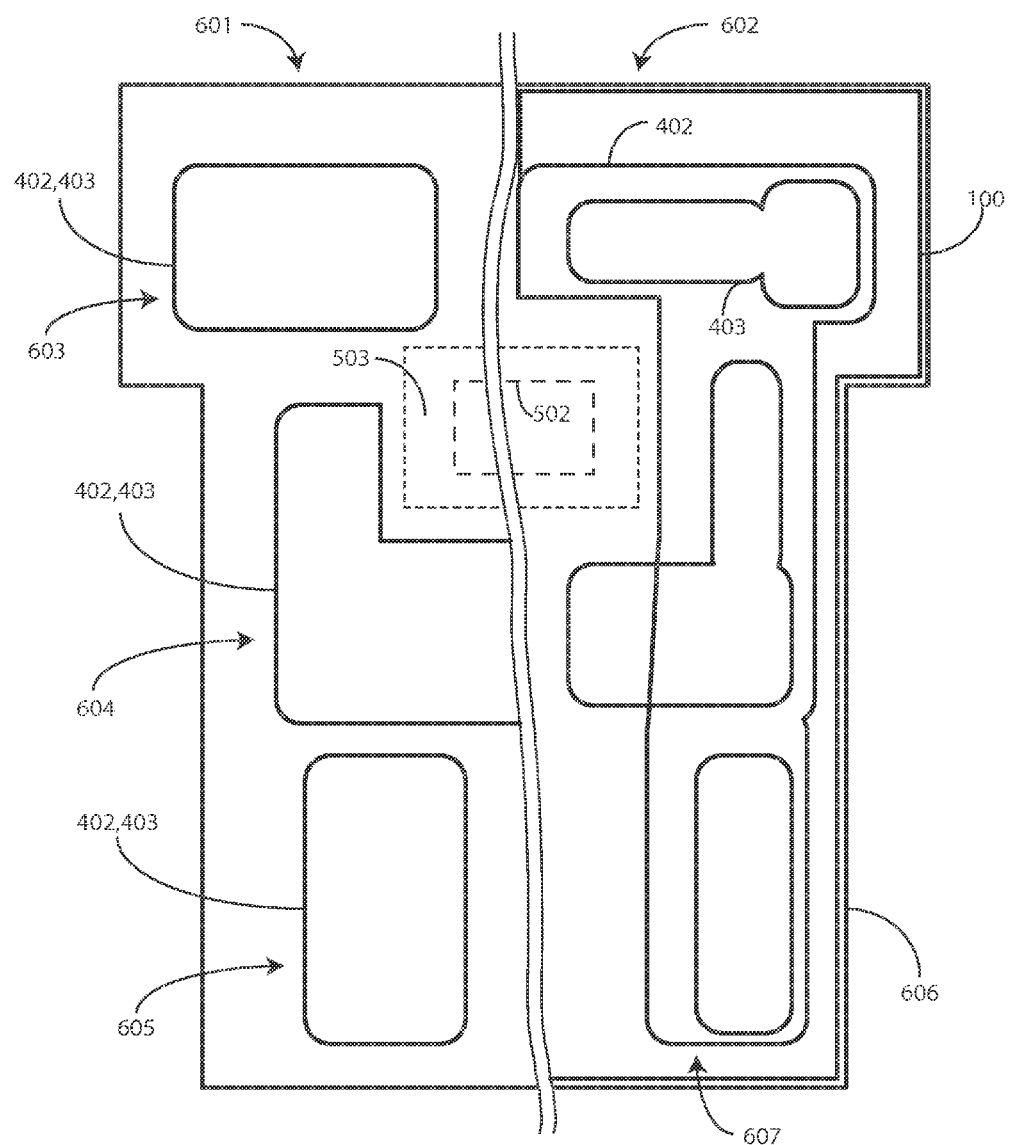
FIG. 6 illustrates sections of exemplary patient warming devices showing possible placement of components, including the film layer, reflective coating, and thermally absorptive coating in accordance with one or more embodiments of the invention.

As will be described below with reference to FIG. 6, in one or more embodiments a reflective material 102 can be selectively applied to only portions of the film layer 100. For example, when only selective reflection of thermal heat is desired, the reflective material 103 can be applied along sub portions of the film layer 100. Further, the reflective material 102 can be applied in accordance with predefined patterns, such as those that correspond to a patient's bodily outline.

In one or more embodiments, a thermally absorptive coating 103 is disposed on the film layer 100 on a side 104 opposite the reflective side 101. The thermally absorptive coating 103 is configured to receive incident light and convert the received light to heat. The thermally absorptive coating 103 can be applied in a variety of ways. For example, in one embodiment the thermally absorptive coating can be vapor deposited along the film layer 100. In another embodiment, the thermally absorptive coating 103 can be printed, screened, or sputtered along the film layer 100. In another embodiment, the thermally absorptive coating 103 can be painted along the film layer 100.

The materials used to form the thermally absorptive coating 103 can also vary. In one embodiment, for example, the thermally absorptive coating 103 can be a paint, which has a color configured to absorb at least a predetermined spectrum or color of light. In one embodiment where paint is used, the paint comprises an ultra flat matte black paint configured to absorb substantially the entire visible spectrum. In another embodiment, the paint can be configured to optimally absorb only a predefined spectrum of light, such as the ultraviolet spectrum.

In another embodiment, the thermally absorptive coating 103 can be a rubberized, plasticized, or polymerized coating. Such a coating can be configured, as was the case with the paint, to have a color or other characteristic that is configured to absorb all or a predefined spectrum of light. Other materials can be used as well, including materials comprising carbon black, dark metal or thermally conductive metal layer materials, or exotic materials such as a thin coating of multi-walled carbon nanotube materials. Such nanotube coatings are effective in that they can be configured to absorb as much as 99.5 percent of the light that hits them. However, such sophisticated materials are generally not required for most applications. In many instances, a matte, flat, black coating, be it paint, ink, plastic, metal, or lacquer, will significantly improve the performance of blankets and drapes configured in accordance with embodiments of the invention as compared to conventional blankets and drapes.

The shape of the film layer 100 can be configured in any of a number of ways. In the illustrative embodiment of FIG. 1, the film layer 100 is configured in a T-shape, which is suitable for forming a surgical drape. In other embodiments, the film layer 100 can be cut to other shapes in accordance with a particular application or to cover any selected portion of a patient.

Figure 2:
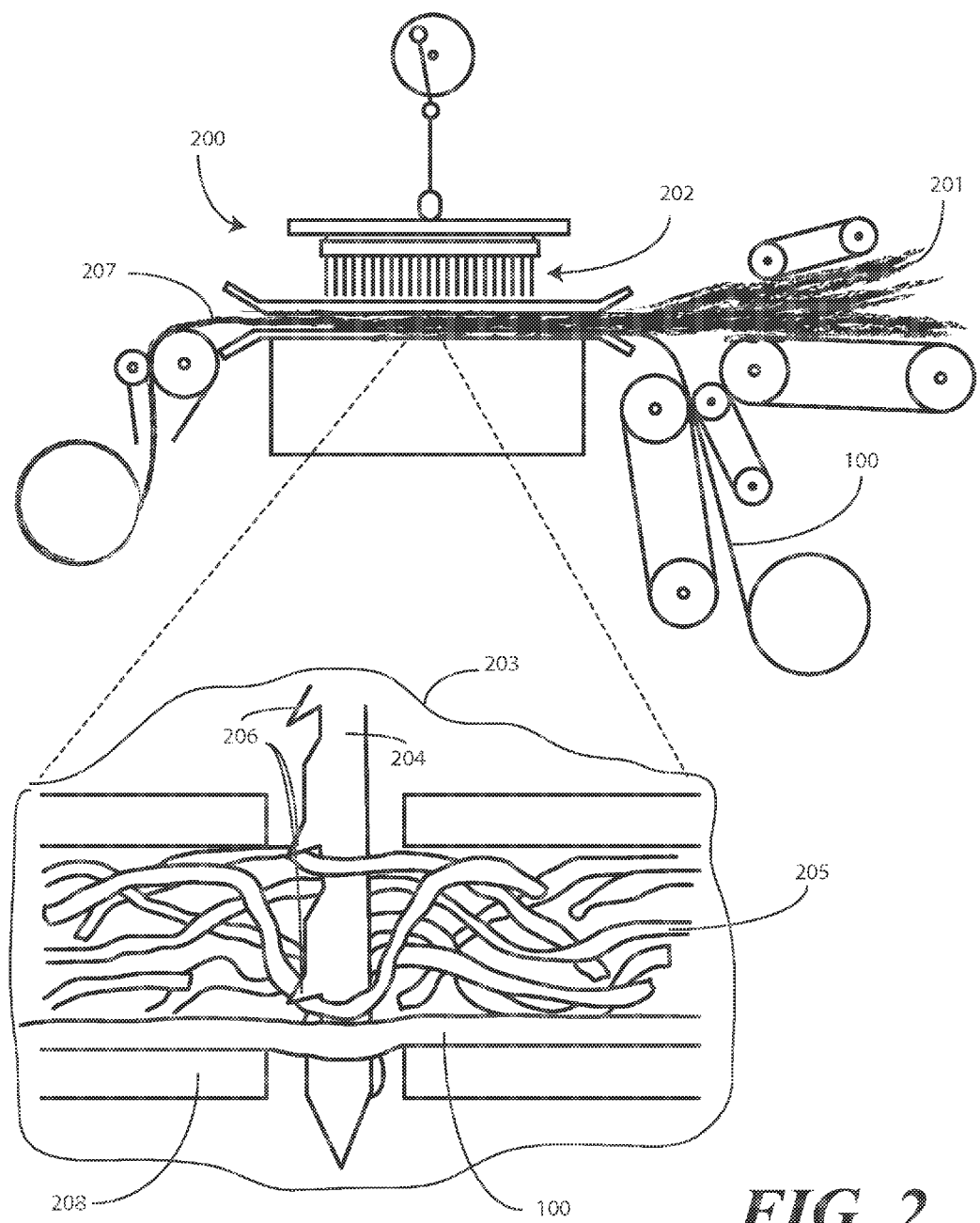
FIG. 2 illustrates one method of forming a blanket configured in accordance with one or more embodiments of the invention.

In one embodiment, a patient warming blanket can be formed by way of a needle punching process. Turning now to FIG. 2, illustrated therein is one such process.

As shown in FIG. 2, the film layer 100 is being fed into a needle punch machine 200. Simultaneously, a non-woven bunch of interlocking fibers 201 are fed into the needle punch machine 200. The non-woven bunch of interlocking fibers 201 can be fund from a spunbond or carded web.

A plurality of barbed felting needles 202 then pass through the web of fibers and through the film layer 100, thereby punching a hole in the film layer 100 and causing one or more fibers to remain "stuck" in the newly formed hole. Zoomed view 204 illustrates this process. Felting needle 204 is passing through the web 205 of interlocking fibers 201. The felting needle 204 is additionally punching through the film layer 100. One or more barbs 206 catch the fibers and cause them to pass through the hole with the felting needle 204. When the needle is withdrawn, the film layer 100 acts as a stripper plate and strips the fibers from the barbs 206. Accordingly, the fibers remain stuck within the formed hole. When this process is repeated many times, a series of fibers stuck in the holes form an isotropic batting that feels like the surface of an ordinary blanket. The result is a patient warming blanket 207 that exits the needle punch machine 200. The patient warming blanket 207 can be spooled and then cut as desired in accordance with the description above.

While the film layer 100 can extend across substantially the entire patient warming blanket 207, it will be clear to those of ordinary skill in the art having the benefit of this disclosure that embodiments of the invention are not so limited. In one or more embodiments, the interlocking fibers 201 can extend beyond the film layer 100. Where this occurs, a stripper plate 208 can be used to pull the interlocking fibers 201 from the barbs 206 to form portions of the patient warming blanket 207 without the film layer 100 therein. These portions would be configured simply as needle punched material in accordance with well known needle punch processes.

The film layer 100 can be oriented with either the reflective side (101) or the opposite side (104) first receiving the felting needle 204. For example, in one embodiment, the opposite side (104), upon which the thermally absorptive coating 103 is deposited, is oriented down such that the felting needle 204 pushes the fibers distally through the thermally reflective side (101) to the thermally absorptive side. This configuration leaves more of the reflective side (101) exposed. When used as a patient warming blanket, the reflective side (101) can be placed adjacent to the patient. As more reflective material is exposed, more of the patient's body heat will be reflected by the reflective side (101).

In another embodiment, the reflective side (101) is oriented down such that the felting needle 204 pushes the fibers through to the reflective side (101). This configuration leaves more of the absorptive side exposed. When used as a patient warming blanket, the reflective side (101) can again be placed adjacent to the patient. As more batting is disposed along the patient side, the blanket will feel softer, and perhaps more comfortable, to the patient. While an anesthetized patient may not care much about comfort, a recuperating patient may prefer to have more batting between the film layer 100 and the skin. Further, with more thermally absorptive material (103) exposed, more light can be absorbed and converted to heat, thereby warming the patient. The decision regarding which side is first contacted by the felting needle 204 will depend upon application and desired heating performance.

Figure 3:
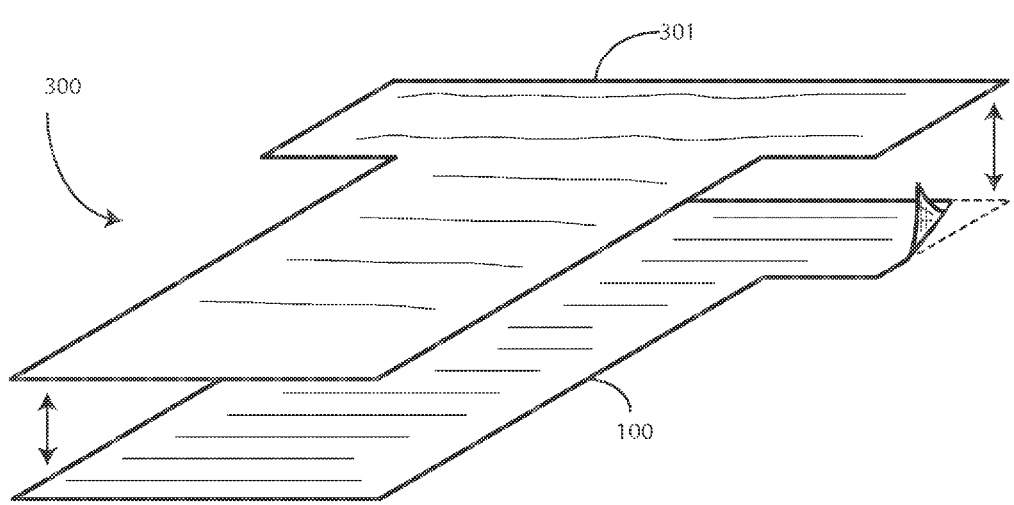
FIG. 3 illustrates one method of forming a drape configured in accordance with one or more embodiments of the invention.

In another embodiment, a patient warming drape can be formed by way of a lamination process. Turning now to FIG. 3, illustrated therein is one such process. Specifically, a film layer 100 having a thermally reflective side (101) and a thermally absorptive side (103) is laminated to a layer of non-woven fabric 301 to form a patient warming drape 300.

As shown in FIG. 3, in one embodiment the layer of non-woven fabric 301 can be configured to be the same size and shape as the film layer 100. In other embodiments, such as those described below with reference to FIG. 6, the layer of non-woven fabric can be configured to cover an area greater than that spanned by the film layer 100. In this latter embodiment, the film layer 100 is only configured to cover portions of the patient warming drape 300.

Examples of non-woven fabrics suitable for the non-woven fabric 301 of FIG. 3 include spunlace, spunbond, and blends of polyester, polypropylene, and/or polyethelyne, as well as combinations thereof. Suppliers of such materials include Cardinal Health in Dublin, Ohio, Kimberly Clark in Neena, Wis., Molnycke Health Care in Newtown, Pa., and Precept Medical Products, Inc., in Arden, N.C. This list is illustrative only. Other materials suitable for use will be obvious to those of ordinary skill in the art having the benefit of this disclosure. The non-woven fabric 301 can be a disposable material, and optionally can include and water resistant lining that prevents the passage of fluids through the patient warming drape 300. In one embodiment, the patient warming drape 300 is configured to be reusable after an appropriate cleaning and sterilization process has been applied. (The same is true for the patient warming blanket (207) described above.)

As with the patient warming blanket (207) described above, the film layer 100 can be oriented with either the thermally reflective side (101) or the thermally absorptive side (103) oriented towards the non-woven fabric 301. In another embodiment, a layer of the non-woven fabric 301 can be disposed on both sides of the film layer 100.

The film layer 100 and non-woven fabric 301 can be laminated together in a variety of ways. In one embodiment, a simple adhesive can be applied to the film layer 100. The non-woven fabric 301 can be adhered to the adhesive. In another embodiment, where the thermally absorptive side (103) is oriented facing the non-woven fabric 301, the thermally absorptive coating (104) can be used as an adhesive to adhere the non-woven fabric 301 to the film layer 100. Other laminating techniques can be used as well, including hotmelt laminating techniques, thermal laminating techniques, and so forth.

Figure 4:
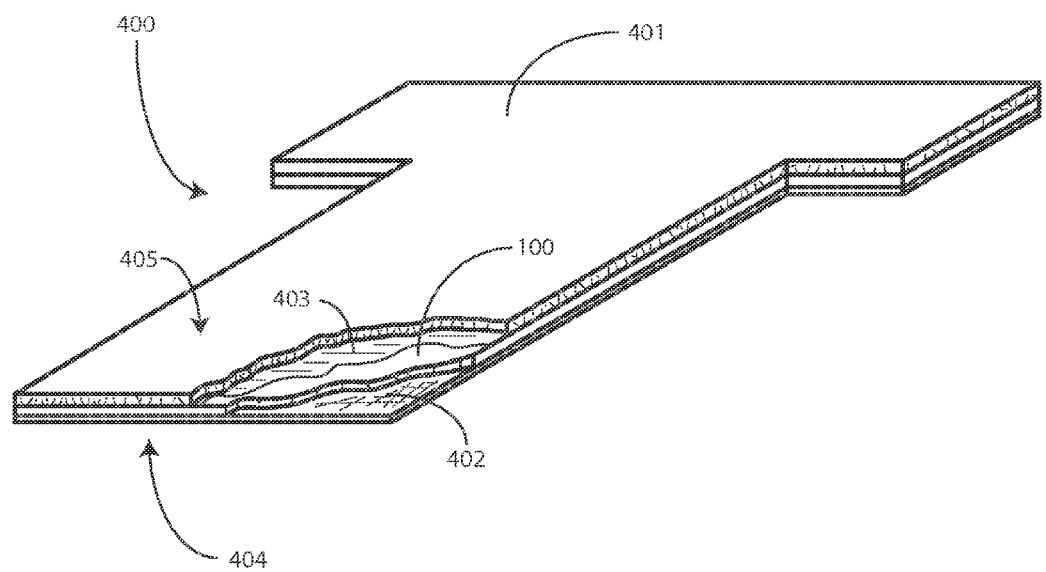
FIG. 4 illustrates one patient warming device configured in accordance with one or more embodiments of the invention.

Turning now to FIG. 4, illustrated therein is a sectional view of a patient warming device 400 configured in accordance with one or more embodiments of the invention. The patient warming device 400 is shown sectionally so that each of the layers and components can be seen. The patient warming device 400 of FIG. 4 can be either a patient warming blanket (207) or patient warming drape (300), depending upon how the top layer 401 is formed. In the case of a patient warming blanket (207), the top layer 401 will be formed by a needle punch process as described with reference to FIG. 2. In the case of a patient warming drape (300), the top layer 401 will be formed by laminating a non-woven fabric (301) to the film layer 100.

As shown in FIG. 4, the film layer 100 forms the core of the patient warming device 400. The film layer 100 is integrated with the top layer 401, either by a needle punch process or laminating process as previously described. The film layer 100 has a thermally reflective side 404 and a thermally absorptive side 405. In one embodiment, the thermally reflective side 404 is formed by depositing a thermally reflective layer of material 402 on the film layer 100. Similarly, the thermally absorptive side 405 is formed by applying a thermally absorptive coating 403 along the film layer 100 opposite the thermally reflective side 404. In the illustrative embodiment of FIG. 4, the patient warming device 400 is physically configured as a drape, although other configurations are also possible. As previously described, the patient warming device 400 can be cut, stitched, and sewn to form any number of devices, including blankets, robes, stockinettes, hats, wraps, and so forth.

Figure 5:
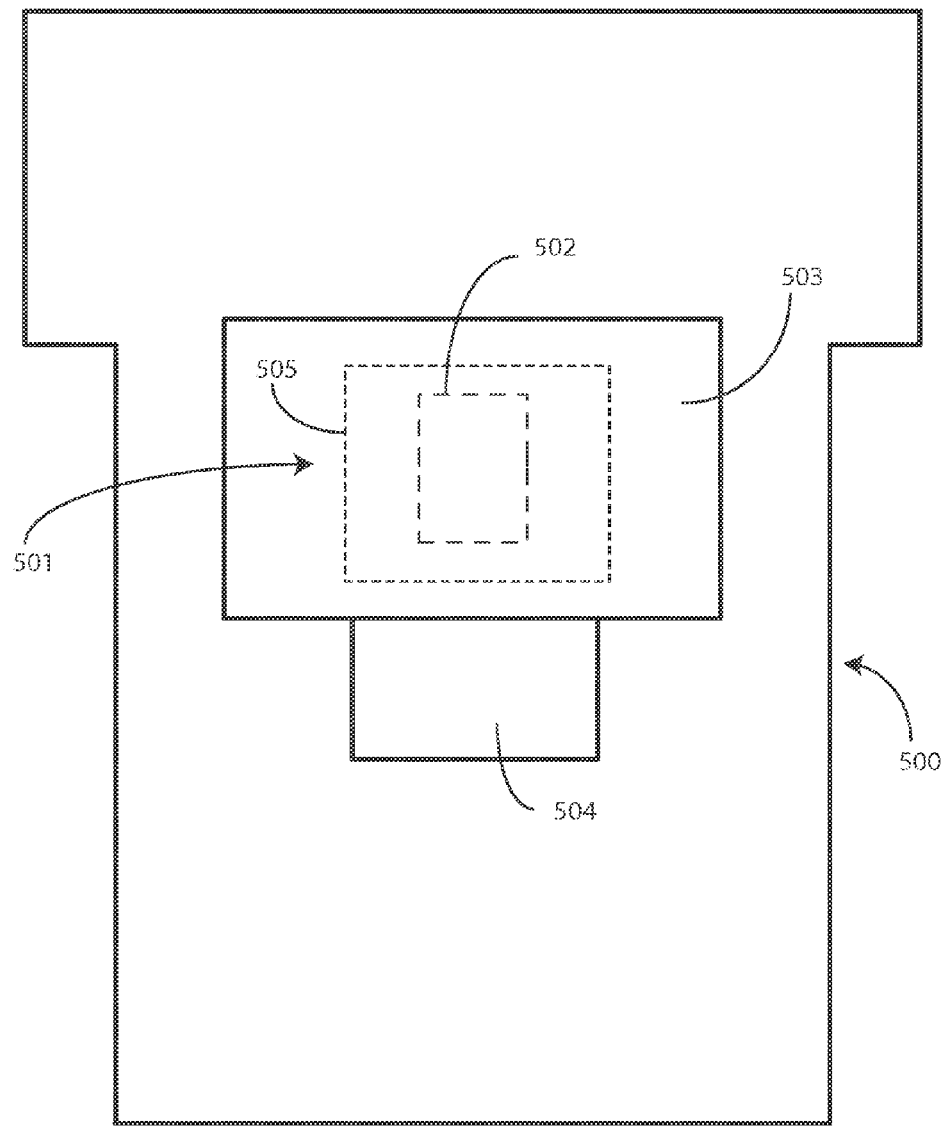
FIG. 5 illustrates one patient warming device configured with a fenestration and including a film layer configured in accordance with one or more embodiments of the invention.

In one embodiment, the patient warming device 400 is configured as a surgical drape. Turning now to FIG. 5, illustrated therein is one such surgical drape 500. The surgical drape 500 includes a fenestration window 501 through which a surgeon can perform a surgical procedure on a patient. Fenestration windows in surgical drapes are described generally in commonly assigned U.S. application Ser. No. 12/008,818, filed Jan. 14, 2008, and Ser. No. 13/005,778, filed Jan. 13, 2011, each of which is incorporated herein by reference for all purposes.

The surgical drape 500 of FIG. 5 includes all of the components of the patient warming device (400) described with respect to FIG. 4. These components include a top layer (401) of a non-woven fabric (301) integrated with a film layer (100) by a laminating process in one embodiment. As previously described, the film layer (100) has both a thermally absorptive layer (403) and a thermally reflective layer (402).

To make the surgical drape 500 simpler for a surgeon to use, the illustrative surgical drape 500 of FIG. 5 also includes an opening or fenestration 502 disposed in a fenestration window 501 that is configured for positioning over a surgical site. The fenestration 502 may be centrally located in the surgical drape 500 or may be positioned at other non-central locations. The illustrative fenestration 502 of FIG. 5 is rectangular. However, it will be clear to those of ordinary skill in the art having the benefit of this disclosure that embodiments of the invention are not so limited. For example, the fenestration 502 may be configured as other shapes that would be suitable for positioning over a surgical site. In addition to the fenestration 502, the fenestration window 501 can also include one or more panels 503,504. The panels 503,504 can be configured as reinforcement panels or for absorbing fluids. The panels 503,504 may also be adapted for use as an anti-skid mat to prevent instruments from sliding on the surgical drape 500.

Where the surgical drape 500 includes a fenestration 502, in one embodiment the film layer (100) is configured such that no film is present in a separation region 505 defined about the fenestration 502. Accordingly, the separation region 505 is formed only from the non-woven fabric (301) and includes neither the thermally reflecting layer (402) nor the thermally absorptive layer (403). A reason for including the separation region 505 in one or more embodiments is to prevent arcing from cauterization equipment used during surgery. For example, where the thermally reflecting layer (402) comprises a metalized layer deposited on a film layer (100), it is conceivable that a cauterization device might arc to the metal. However, the inclusion of a separation region 505 precludes this. In one embodiment, the separation region 505 has a width of between three and four inches, although other widths may also be used.

In one or more embodiments, patient warming blankets (207), patient warming drapes (300), or surgical drapes (500) configured in accordance with embodiments of the invention may include a film layer (100) that spans less than the entirety of the overall device. Turning now to FIG. 6, illustrated therein are some exemplary sections 601,602 of patient warming devices configured in accordance with embodiments of the invention where one or more of the film layer 100, the thermally reflecting layer 402, or the thermally absorptive layer 403 span only one or more portions of the device.

Beginning with section 601, in this illustrative section, the film layer 100 has been configured to span the entirety of the non-woven fabric 301. The film layer 100 and non-woven fabric 301 are integrated together by way of a laminating process.

While the film layer 100 spans the entirety of the non-woven fabric 301, the thermally reflective layer 402 and thermally absorptive layer 403 span only portions of both the film layer 100 and the non-woven fabric 301. In this illustrative embodiment, the thermally reflective layer 402 and thermally absorptive layer 403 generally overlap, and are configured to cover three particular portions 603, 604, 605 of the non-woven fabric. The first portion 603 corresponds to a patient's shoulder, while the second portion 604 corresponds to a patient's torso. The third portion 604 corresponds to a patient's leg. These portions are illustrative only. Where a fenestration 502 is included, neither the thermally reflective layer 402 nor the thermally absorptive layer 403 is present in the separation region 505.

In section 602, the film layer 100 is configured to span less than the entirety of the fabric layer 606, which is formed in this illustrative embodiment by a needle punched process. The film layer 100 spans only a portion 607 of the fabric layer 606. As with section 601, the portion 607 of 602 spanned by the film layer 100 corresponds to a body-covering portion, generally following the contour of a patient's torso, although other portion geometries are possible as well.

In section 602, rather than overlapping, the thermally reflective layer 402 and thermally absorptive layer 403 span different portions of the film layer 100. In this illustrative embodiment, the thermally absorptive layer 403 spans less area than does the thermally reflective layer 402. Accordingly, three different levels of warming are provided: a first level where only the fabric layer 606 is present; a second level where one of the thermally reflective layer 402 or the thermally absorptive layer 403 is present but the other is not; and a third level where both the thermally reflective layer 402 and thermally absorptive layer 403 are present. As will be understood by those of ordinary skill in the art having the benefit of this disclosure, a myriad of combinations and permutations of reflective warming, absorptive warming, and conventional warming can be achieved with different physical configurations of the various layers.

Figure 7:
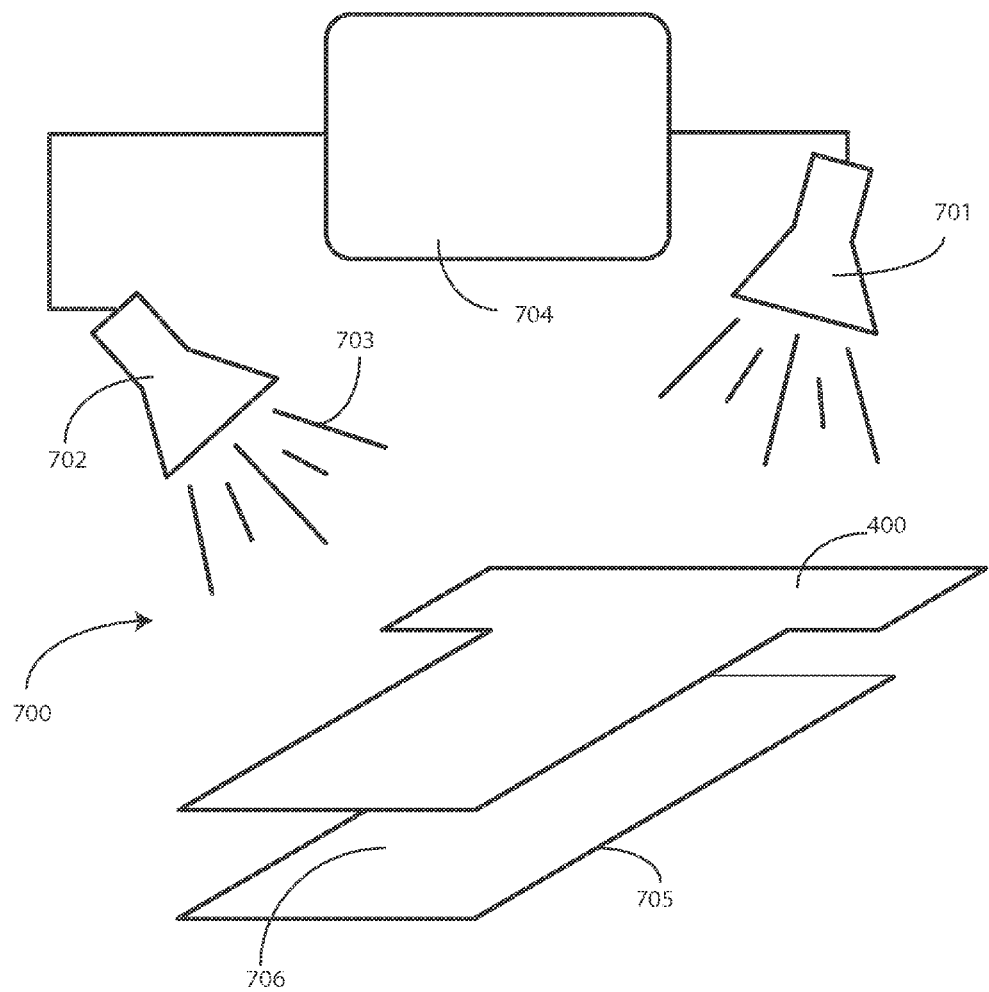
FIG. 7 illustrates a block diagram of one patient warming system configured in accordance with one or more embodiments of the invention.

Turning now to FIG. 7, illustrated therein is one embodiment of a patient warming system 700 configured in accordance with one or more embodiments of the invention. In addition to a patient warming device 400, one or more light sources 701,702 are configured to deliver light to the thermally absorptive layer (403) of the patient warming device 400. Specifically, when the one or more light source 701,702 deliver light 703 to the patient warming device 400, the thermally absorptive layer (403) is configured to absorb the light 703 and transform it into heat, thereby warming the film layer (100) and thus the patient warming device 400.

In one embodiment, the one or more light sources 701,702 comprise incandescent or fluorescent lights. In another embodiment, the one or more light sources 701,702 comprise special lighting, such as ultraviolet lighting. The patient warming device 400 can be configured to work with existing lighting in procedure rooms, such as operating rooms. Alternatively, the patient warming system 700 can be configured with special lights to enhance the patient warming process. Examples of light sources 701,702 suitable for use in the patient warming system 700 include the following: a 375-watt BR40 shatterproof infrared lamp; a 40-watt infrared PAR20 halogen light; and a shatter-proof 100 watt high-pressure sodium light. Other types of light sources 701,702 will be readily apparent to those of ordinary skill in the art having the benefit of this disclosure.

In one or more embodiments, to control the amount of light 703 delivered to the patient warming device 400, a control module 704 is provided that is operable with the one or more light sources 701,702. The control module 704 can be configured to selectively vary the amount of light 703 in a variety of ways. For example, in one embodiment the control module 704 is configured to vary the amount of light 703 by varying the active duty cycle of each of the light sources 701,702. A temperature sensor (not shown) may be disposed beneath the patient warming device 400. By monitoring the temperature through the temperature sensor, the control module 704 can be configured to selectively turn on and off the light source 701,702 by varying the duty cycle.

In another embodiment, the control module 704 can be configured to selectively vary the amount of light 703 delivered to the patient warming device 400 by varying the intensity of the light 703. Said differently, by varying the power, voltage, and/or current delivered to each light source 701,702, the intensity of the light 703 can be varied, thereby controlling the amount of heat converted by the thermally absorptive layer (403) of the patient warming device. In another embodiment, the intensity can be varied by selectively altering the distance between the light sources 701, 702 and the patient warming device 400. This can be done when the control module 704 is configured to control motors, servos, or other motion devices to move the light sources 701,702 closer to, and further from, the patient warming device 400. Of course, combinations of these techniques could also be used.

In one embodiment, the patient warming system 700 further includes a patient underlayer 705 configured for placement beneath a patient when the patient is on a bed or operating table. The patient underlayer 705 can be a simple film layer, a patient warming blanket, a patient warming drape, or other device. In one embodiment, the patient underlayer 705 is configured with at least one reflective side 706. The reflective side 706 can be used to reflect the patient's body heat back during a medical procedure. When both the patient warming device 400 and the patient underlayer 705 are used, a thermal cocoon is effectively formed about the patient.

Figure 8:
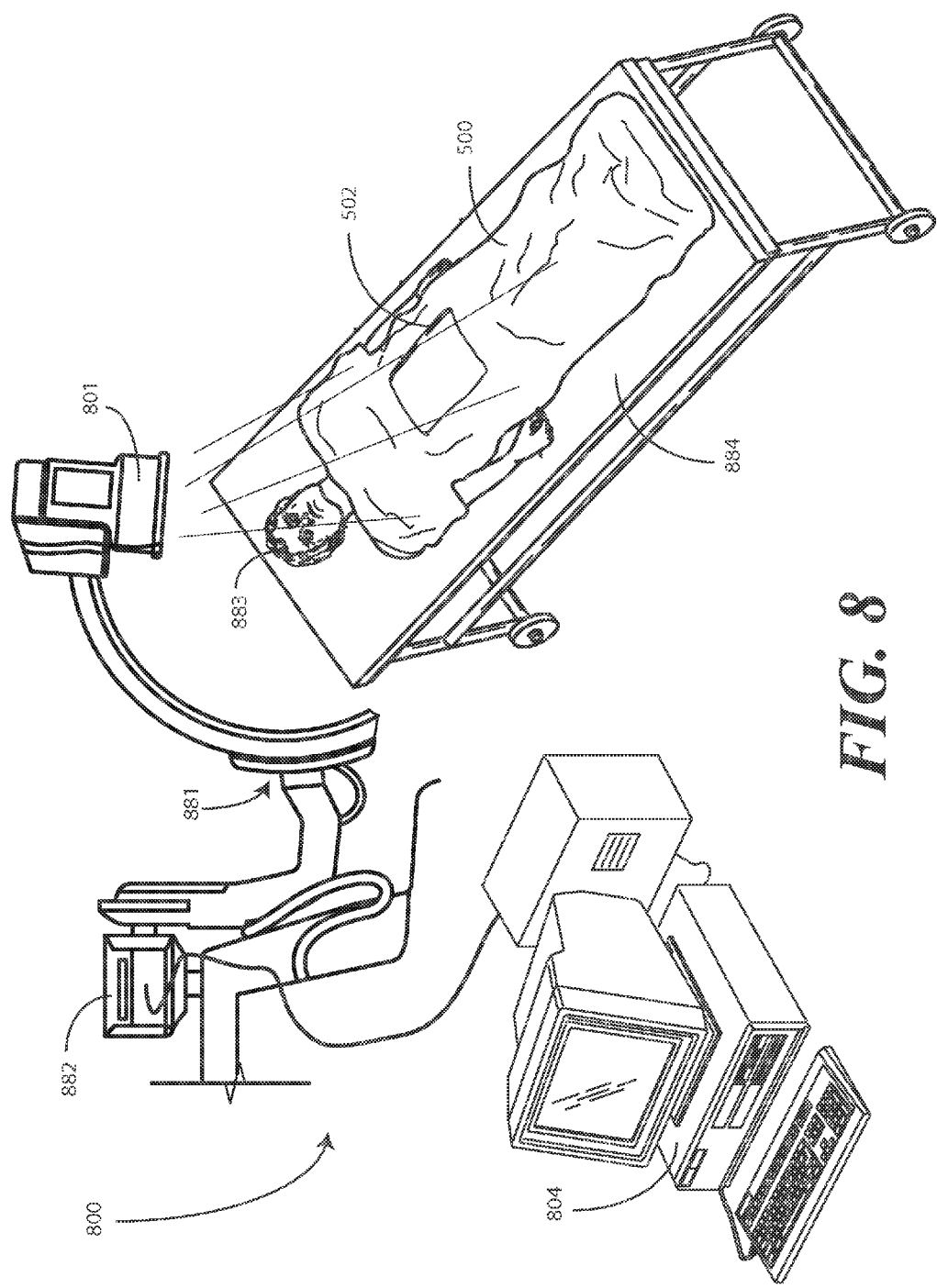
FIG. 8 illustrates a patient warming system in use in accordance with one or more embodiments of the invention.

Turning now to FIG. 8, illustrated therein is one embodiment of a patient warming system 800 configured in accordance with one or more embodiments of the invention in use. The control device 804, configured here as a computer terminal, is operative with an infrared light source 801 to vary the intensity of light 803 being delivered to a surgical drape 500 configured in accordance with embodiments described herein. In this illustrative embodiment, the control device 804 varies the intensity of light 803 in two ways: first, by controlling a motor 881 to move the light closer to, and farther from, the surgical drape 500 as necessary. Second, the control device 804 varies the intensity of light 803 by selectively dimming the light source 801 by way of a dimmer 882. In this illustrative embodiment, the surgical drape 500 includes a fenestration 502 and has been placed upon an anesthetized patient 883 awaiting a surgical procedure on an operating table 884.

Figure 9:
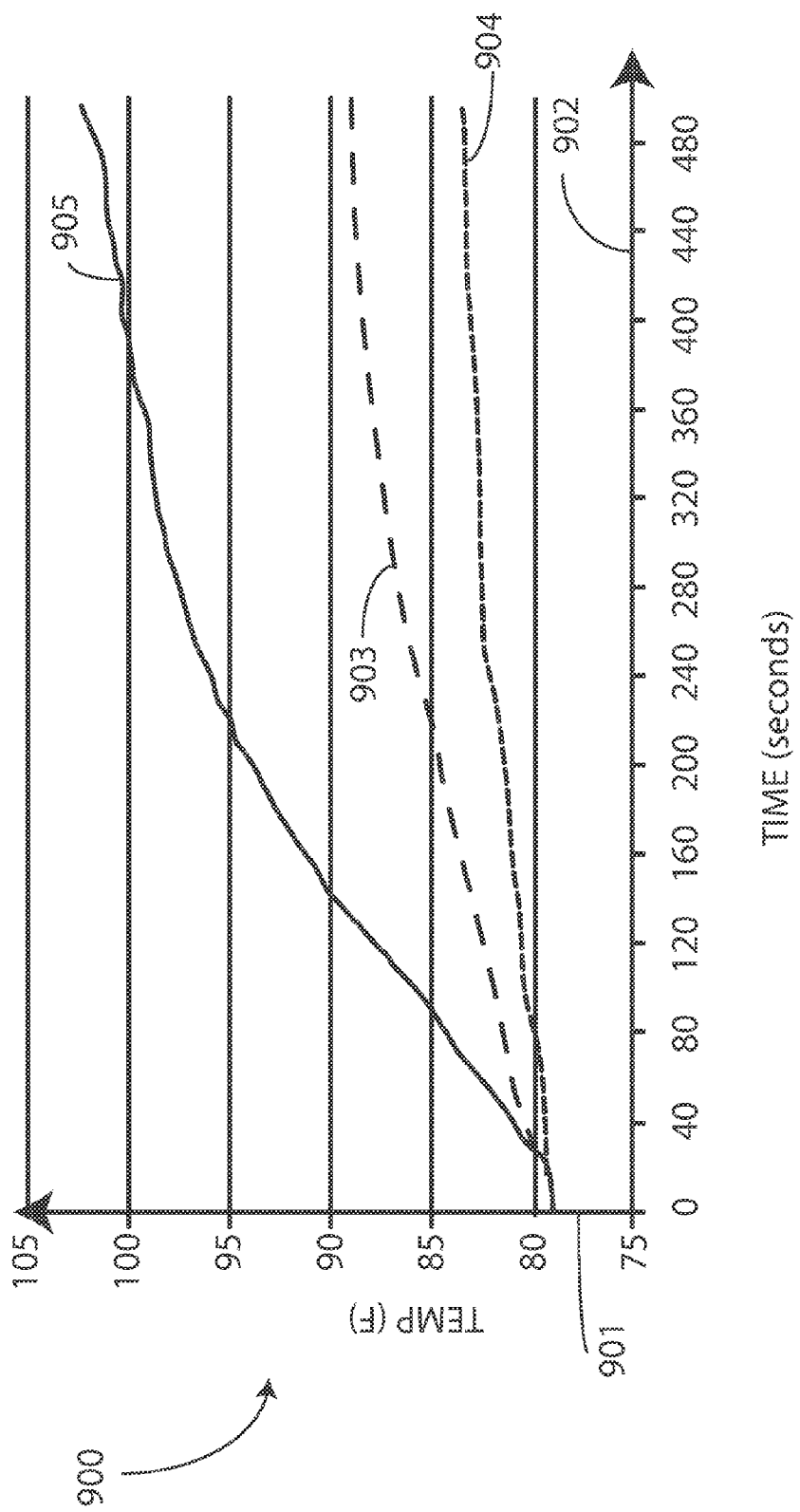
FIG. 9 illustrates a graph showing performance of a patient warming device configured in accordance with one or more embodiments of the invention.

Experimental testing has shown superlative results of patient warming systems configured in accordance with embodiments of the invention when compared to conventional blankets and drapes. Turning now to FIG. 9, illustrated therein is an output graph 900 obtained when a standard incandescent 100-watt bulb was used with a patient warming device. The bulb was placed about twelve inches from the patient warming device and temperature was measured over a 500-second duration, which is represented by axis 902. Temperature is plotted along axis 901.

Curve 903 illustrates the temperature measured beneath a conventional blanket. Curve 904 illustrates the temperature measured beneath a blanket that includes a reflective layer, similar to that described in U.S. Pat. No. 4,945,924 to Poettgen. Curve 905 illustrates the temperature measured beneath a patient warming device (400) that includes both a thermally reflective layer (402) and a thermally absorptive layer (403) as described above. As shown, after approximately 400 seconds, the patient warming device (400) performed more than eighteen percent better than the conventional blanket and more than twenty-one percent better than the reflective blanket.

It is clear from the output graph 900 of FIG. 9, that patient warming devices configured in accordance with embodiments of the present invention offer superior warming performance when compared to prior art blankets configured with, or without, a reflective layer. Another advantage offered by embodiments of the invention is that this improved warming performance is obtained by a blanket or drape that is in fact thinner than prior art systems.

Illustrating by example, the conventional blanket used to obtain curve 903 has a thickness of 0.055 inches. By contrast, the patient warming device configured in accordance with embodiments described herein that was used to obtain curve 905, which comprised a single ply mylar layer with matte black coating laminated by an adhesive layer to a layer of non-woven fabric (20-gram black scrim) to form a patient warming drape as described above with reference to FIG. 3 measured only 0.0165 inches in thickness. The eighteen percent increase in warming was, therefore, achieved with a blanket that was less than one third the thickness of the prior art blanket. Depending upon the laminating process used, when using scrim having a weight between 20-gram to 45-gram as the material layer, bonded to a thermally reflective layer with a thermally absorptive layer, the overall thickness can be reduced to between about 0.011 and about 0.013 inches. Even when a thick adhesive is used, the cumulative thickness of the blanket will be less than about 0.02 inches, which is far thinner than prior art blankets used to warm patients. "About" is used to indicate 0.02 inches plus or minus normal manufacturing tolerances.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A patient warming blanket, comprising:
   a film layer having a thermally reflective layer;
   a thermally absorptive coating disposed along a side opposite the thermally reflective side; and
   non-woven fibers needle-punched through the film layer;
   the thermally absorptive coating selectively disposed on only portions of the film layer.

2. The patient warming blanket of claim 1, wherein the film layer comprises a polyester film.

3. The patient warming blanket of claim 2, wherein the polyester film comprises polyethelyene terepthalate.

4. The patient warming blanket of claim 1, wherein the thermally reflective layer comprises a metalized layer.

5. The patient warming blanket of claim 4, wherein the metalized layer comprises metalizing only on one or more portions of the film layer.

6. The patient warming blanket of claim 1, wherein the thermally absorptive coating comprises a matte black coating.

7. The patient warming blanket of claim 1, wherein the thermally reflective layer and the thermally absorptive coating span different portions of the film layer.

8. The patient warming blanket of claim 1, wherein the non-woven fibers are needle punched distally through the thermally reflective layer.

9. The patient warming blanket of claim 1, wherein the thermally absorptive coating is configured to absorb infrared light.

10. The patient warming blanket of claim 1, wherein the thermally absorptive coating is configured to absorb incandescent light.

11. A patient warming system, comprising:
    at least one of a patient warming drape or a patient warming blanket, comprising:
    a film layer integrated with a material layer, the film layer having a thermally reflective side defined by reflective material being selectively placed only along portions of the film layer and a thermally absorptive coating selectively disposed on other portions of the film layer opposite the thermally reflective side; and
    a light source configured to deliver light to the thermally absorptive coating;
    wherein the thermally absorptive coating is configured to absorb the light to warm the film layer.

12. The patient warming system of claim 11, the portions and the other portions non-overlapping.

13. The patient warming system of claim 11, wherein the light source comprises an infrared light source.

14. The patient warming system of claim 11, further comprising a control module, operable with the light source, and configured to selectively vary an amount of the light that is delivered to the thermally absorptive coating.

15. The patient warming system of claim 14, wherein the control module is configured to one of vary a duty cycle of the light source, vary an intensity of the light source, vary a distance between the light source and the film layer, or combinations thereof.

16. The patient warming system of claim 11, further comprising a patient underlayer comprising at least one reflective side.

* * * * *